(12) United States Patent
Crihan

(10) Patent No.: US 6,242,664 B1
(45) Date of Patent: Jun. 5, 2001

(54) STERILIZATION OF MEDICAL WASTE MATERIALS IN AN IMPROVED IRRADIATING FACILITY

(76) Inventor: Ioan G Crihan, 417 E. 64th St. Apt., 4G, New York, NY (US) 10021

( * ) Notice: Subject to any disclaimer, the term of this patent is extended or adjusted under 35 U.S.C. 154(b) by 0 days.

(21) Appl. No.: 08/766,138

(22) Filed: Dec. 17, 1996

(51) Int. Cl.[7] .............................. A62D 3/00; B01D 17/06; A21D 6/00
(52) U.S. Cl. ................ 588/227; 204/158.2; 210/748; 426/240
(58) Field of Search ..................... 588/219, 227; 204/157.15, 158.2; 422/22; 210/748; 426/240

(56) References Cited

U.S. PATENT DOCUMENTS 4,151,419 * 4/1979 Morris et al. .................. 250/453
5,496,295 * 3/1996 Wilfong et al. ................. 604/332
5,545,796 * 8/1996 Roy et al. ....................... 588/4

* cited by examiner

Primary Examiner—Edna Wong

(57) ABSTRACT

A method and equipment for accomplishing same for rapid sterilization of huge quantities of medical waste materials by exposure to a high dose of radiation energy. The radiation sterilizes organic materials destroying insects, molds, bacteria, viruses and other destructive biological vectors. The equipment includes an improved irradiating facility, namely, either a mobile temporary irradiating chamber, or a fixed temporary irradiation chamber with protective walls capable of being assembled or disassembled. The gear is mounted on suitable transportation means.

8 Claims, 4 Drawing Sheets

STERILIZATION OF MEDICAL WASTE MATERIALS IN AN IMPROVED IRRADIATING FACILITY

SUMMARY OF INVENTION

The present invention consists of a method of rapid sterilization, by exposure to high dose of irradiation, of huge quantities of medical waste. The present invention consists also in a method of processing the said type of sterilization at the very place where the medical waste to be sterilized, is located by using either a mobile station or a fixed irradiating chamber with protective walls mounted or dismounted as necessary.

Current method of sterilization, using low doses of energy, has the disadvantage of not permitting the complete sterilization of organic materials, such as the medical waste, at industrial level. At such level, the use of low doses of energy for the sterilization of large quantities of organic material would require too long a period of time. It is one object of this invention to both reduce the time of exposure and to increase considerably the volume of material to be exposed to irradiation, as the best way to use the radiation energy for sterilization at industrial levels.

An exposure to current type of irradiating facilities, mainly of hospital wastes, or municipal wastes, would require too much time for transportation and storage. It is therefore too costly, and creates other unforeseen problems. It is an object of this invention to avoid, mainly, the problems of transportation and of storage before exposure to irradiation of huge quantities of medical waste. This is accomplished either by transporting a mobile irradiating chamber mounted on a transportation means, or transporting only the components of the protective walls of an irradiating chamber to the place where the medical waste material is generated and is sterilized at the site. The advantage of such new type of irradiating facilities would consist also in the possibility of the multiplication of both the mobile irradiating chambers and the fixed ones at the locations of the medical waste materials to be sterilized.

DETAILED DESCRIPTION

The present invention consists in a method of rapid sterilization of huge quantities of medical waste materials either in mobile irradiating chambers, or in fixed irradiating chambers, with protective walls to be assembled or disassembled as required.

The mobile and temporary irradiating chamber is built of protective walls mounted on a transportable means, such as a truck, a train, or a ship, and as such, movable to the very locations of the organic material to be sterilized.

The shielding walls of an irradiating chamber consist of assembly or disassembly of panels made of concrete blocks or plates, similar in shape, but different in size, as the conventional lead bricks used for construction of fixed irradiating chambers. These concrete plates are preferably at least 5 feet in thickness.

The same type of concrete panels could be used to construct a protective shield for a fixed irradiating chamber. Being subject to disassembly, they can be easily constructed or taken apart as needed.

The process of sterilization consists in the following steps. First, the organic materials to be sterilized are distributed onto an endless conveyor system which transports the to-be irradiated organic materials to an irradiation chamber. Then, the materials so conveyed are exposed to high doses of irradiation, of up to 5,000,000 RAD, emitted from a source of cobalt 60 or cesium 137. The exposure to such a high dose of energy shortens the period of time of irradiation necessary for the sterilization through irradiation, of large quantities of waste organic materials.

Figure 1:
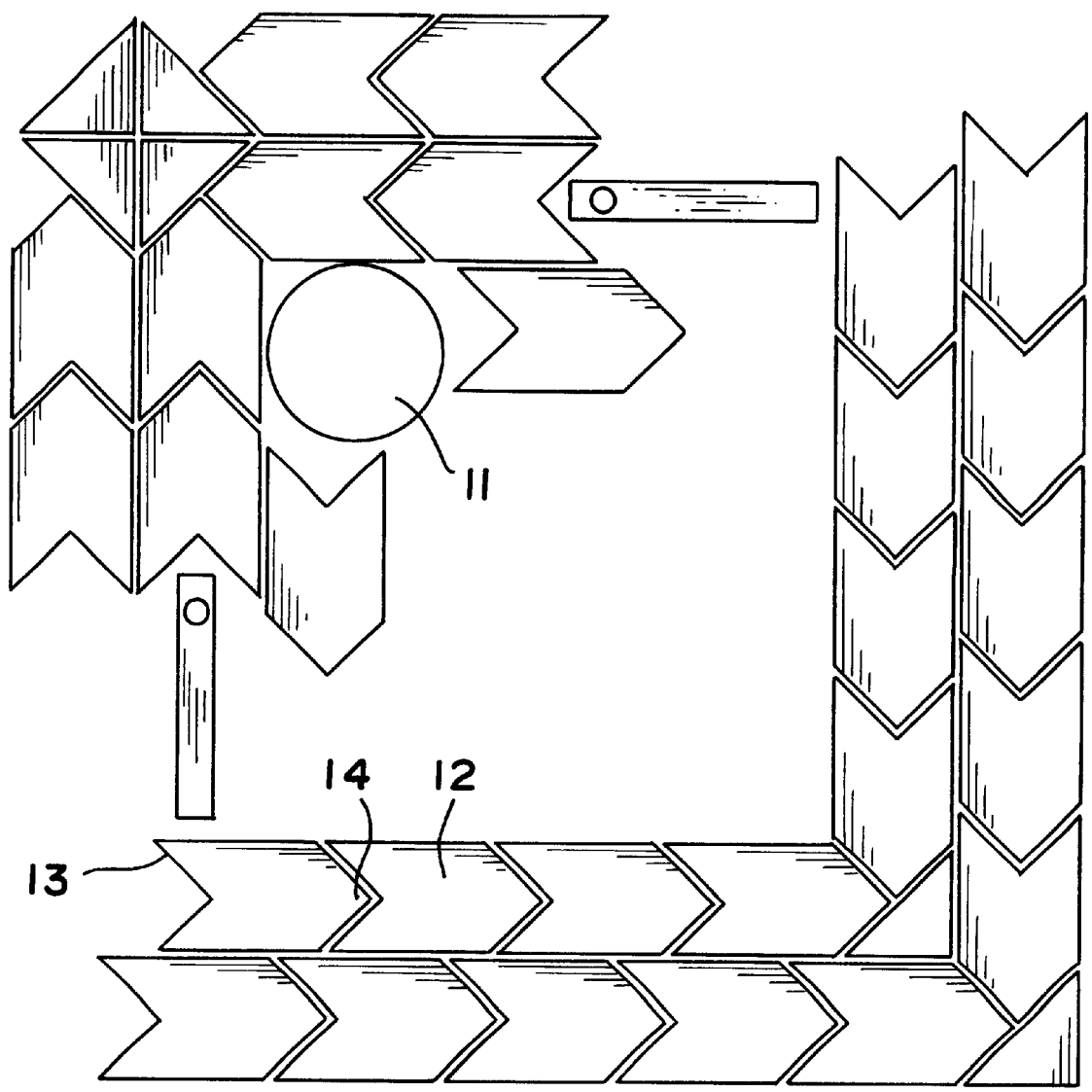
FIG. 1 is a top plan schematic view of the walls for the irradiating chamber.

Attention is directed to FIG. 1 where reference numberal 11 illustrates an irradiation chamber. The chamber 11 is surrounded by at least two rows of concrete blocks 12 which have V-shaped indentations 13 on one side and V-shaped protuberances 14 at each opposite side for dovetailing one to the other. The blocks are thereby detailed to interfit as shown, and suitable locking engagement means may be used to hold the blocks in assembly which upon release permits the rapid disassembly of the same.

Figure 2:
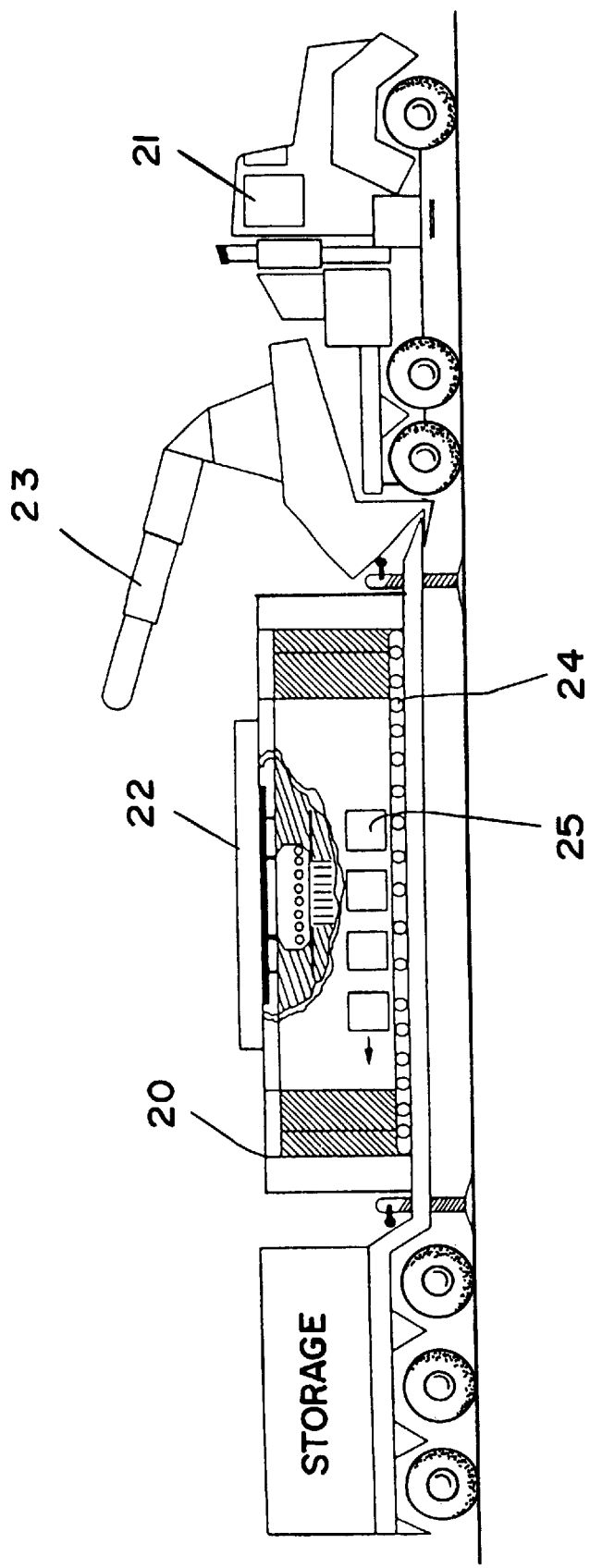
FIG. 2 is a side view showing the transportable irradiating chamber partially fragmented.
Figure 3:
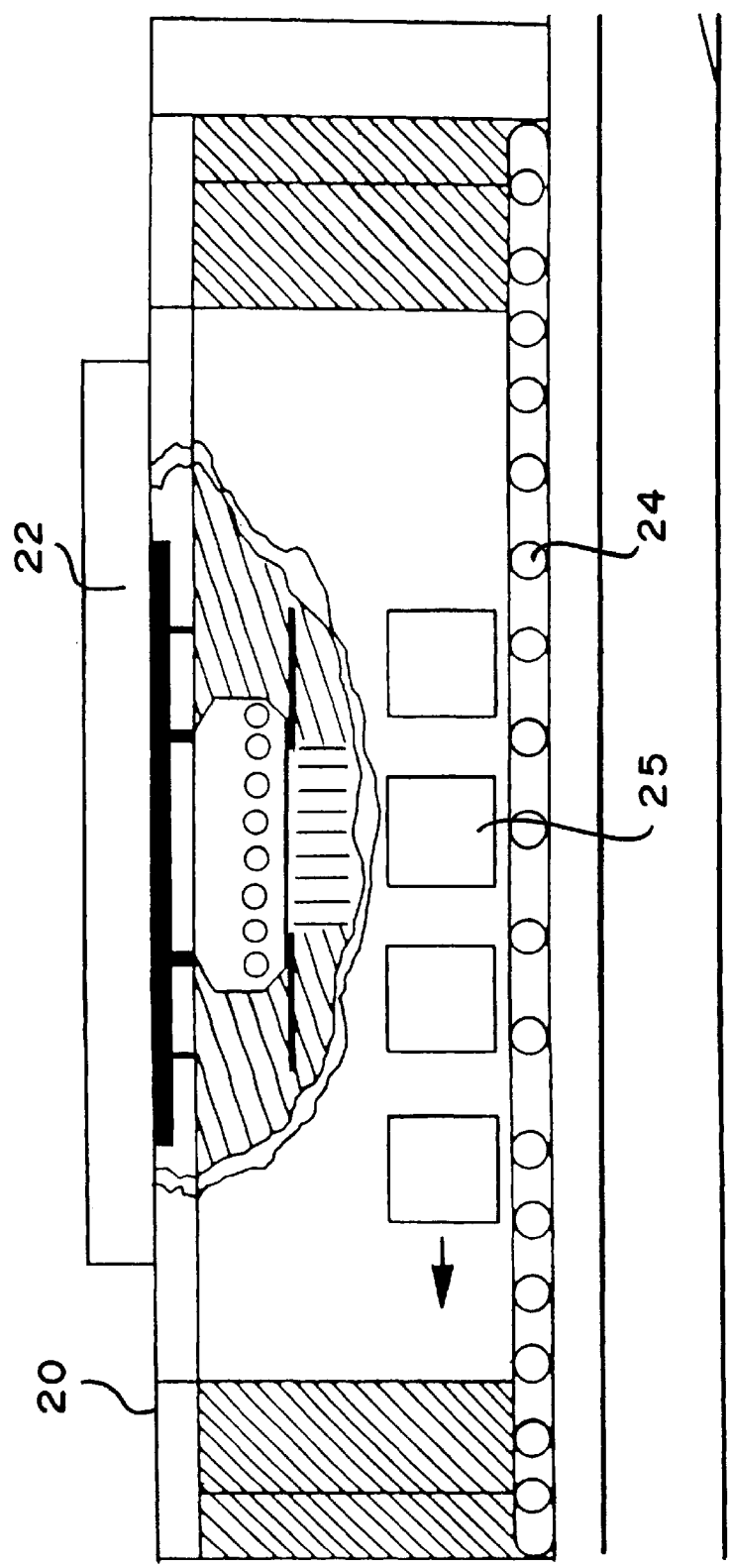
FIG. 3 is an enlarged side view of a portion of FIG. 2.

FIG. 2 shows a transportable trailer 20 having a drawing tractor 21 for bringing the irradiation chamber which is suitably housed in a clad housing to a sterilization site. The trailer has a removable protective roof 22 which may be removed by crane 23 in order to load or unload the radio-isotopic source 22. The trailer has a roller conveyor system 24 upon which containers 25 are moved into and out of the irradiation chamber in a timed sequence for a preselected dwell time in the irradiation chamber. The dwell time can be such as to ensure that each container and its contents receive at least a dosage of 5,000,000 RADs.

Figure 4:
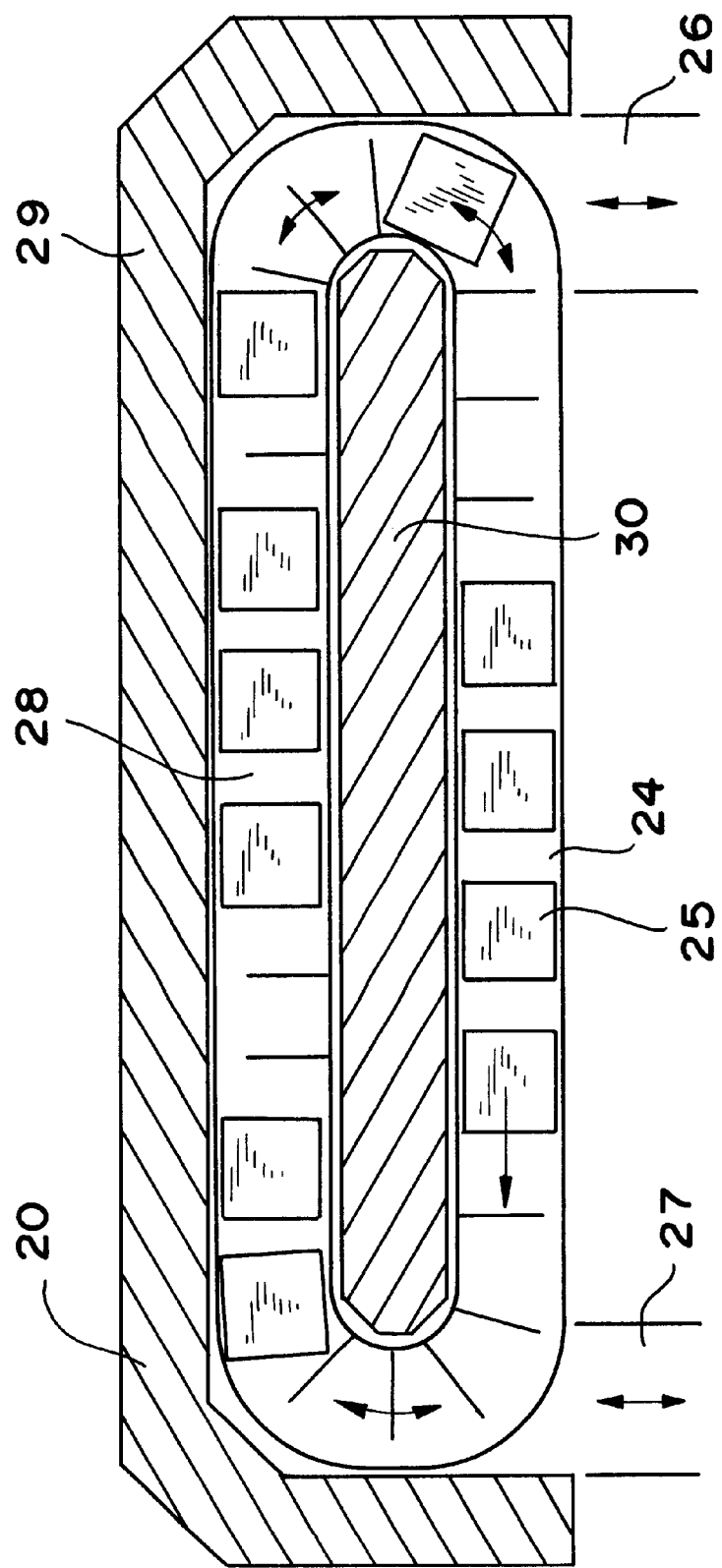
FIG. 4 is a top schematic fragmentary view of FIG. 3.

FIG. 4 shows the containers 25 on the roller conveyor 24 moving into load station 26 and unload station 27. The stations may be reversed. The backside area 28 of the roller conveyor system 24 contains the irradiation source22 . Suitable shielding walls 29 are provided and a shielding wall 30 interposes the conveyor system 24 which in this embodiment is designed to describe an endless path.

The containers 25 are designed to carry the said waste material to be sterilized into and out of the irradiation chamber having the gamma radiation source consisting of cobalt 60 or cesium 137.

What is claimed is:

1. A method of sterilizing organic material including hospital wastes, biohazardous wastes, municipal wastes, sewage, sludge, the destroying enzymes of oil, or the harmful bacteria in food products comprising the steps of assembling a housing from a plurality of interfitting members which can later be disassembled, providing a radiation source of about 5,000,000 RAD therein, providing a conveyor therein, disposing any of the said material on said conveyor and making a single pass adjacent said source of radiation for sterilizing the said material.

2. The method of claim 1 and further including the step of selecting the radiation source from cobalt 60 or celesium 137.

3. The method of claim 1 and further providing the housing with inlet and outlet openings, disposing the conveyor between said openings and disposing the radiation source along one side of the conveyor for sterilizing the material as it passes thereby.

4. The method of claim 1 including the step of mounting the radiation means on a removable component of the housing thereby facilitating the accessing of the same.

5. The method of claim 4 further including the placing of the material to be sterilized in containers for passing the same by the source of radiation.

6. The method of claim 3 wherein the housing is mounted on a transportation means.

7. The method of claim 1 wherein the interfitting members are interfitting blocks.

8. The method of claim 1 wherein the intermitting members are plates.

* * * * *